(12) United States Patent
Chappuis

(10) Patent No.: US 8,979,748 B2
(45) Date of Patent: Mar. 17, 2015

(54) DEVICES AND METHODS FOR TEMPORARILY RETAINING SPINAL ROOTLETS WITHIN DURAL SAC

(76) Inventor: James L. Chappuis, Marietta, GA (US)

( * ) Notice: Subject to any disclaimer, the term of this patent is extended or adjusted under 35 U.S.C. 154(b) by 758 days.

(21) Appl. No.: 12/604,520

(22) Filed: Oct. 23, 2009

(65) Prior Publication Data

US 2011/0098705 A1 Apr. 28, 2011

(51) Int. Cl.
*A61B 1/32* (2006.01)
*A61B 17/02* (2006.01)
*A61B 17/34* (2006.01)

(52) U.S. Cl.
CPC ........... *A61B 17/025* (2013.01); *A61B 17/3423* (2013.01); *A61B 2017/3429* (2013.01); *A61B 17/3431* (2013.01); *A61B 2017/0262* (2013.01)
USPC .......................................... 600/206; 600/235

(58) Field of Classification Search
CPC .... A61B 17/62; A61B 17/66; A61B 17/3423; A61B 17/3431; A61B 2017/3429
USPC ......... 606/53–59, 99; 600/201–204, 206–208
See application file for complete search history.

(56) References Cited

U.S. PATENT DOCUMENTS

| | | | |
|---|---|---|---|
| 5,026,373 A | 6/1991 | Ray et al. | |
| 5,047,030 A | 9/1991 | Draenert | |
| 5,209,450 A | 5/1993 | Grapes | |
| 5,513,838 A | 5/1996 | Van Rossum | |
| 5,649,945 A * | 7/1997 | Ray et al. | 606/167 |
| 5,728,159 A | 3/1998 | Stroever et al. | |
| 5,753,456 A | 5/1998 | Naqui et al. | |
| 5,871,484 A | 2/1999 | Spievack et al. | |
| 5,971,987 A | 10/1999 | Huxel et al. | |
| 6,045,579 A | 4/2000 | Hochshuler et al. | |
| 6,080,193 A | 6/2000 | Hochshuler et al. | |
| 6,143,033 A | 11/2000 | Paul et al. | |
| 6,231,577 B1 | 5/2001 | Canedy | |
| 6,261,295 B1 | 7/2001 | Nicholson et al. | |
| 6,368,325 B1 | 4/2002 | McKinley et al. | |
| 6,379,385 B1 | 4/2002 | Kalas et al. | |
| 6,383,221 B1 | 5/2002 | Scarborough et al. | |
| 6,425,920 B1 | 7/2002 | Hamada | |
| 6,517,544 B1 | 2/2003 | Michelson | |

(Continued)

FOREIGN PATENT DOCUMENTS

AT 0490517 A1 6/1992
GB 2157177 A 10/1985

(Continued)

OTHER PUBLICATIONS

Brodie, et al., "An Injectable Cementing Screw for Fixation in Osteoporotic Bone," pp. 216-220.

*Primary Examiner* — Eduardo C Robert
*Assistant Examiner* — Stuart S Bray
(74) *Attorney, Agent, or Firm* — McHale & Slavin, P.A.

(57) ABSTRACT

Devices and methods for temporarily retaining spinal rootlets within a dural sac are provided. In this regard, a representative device includes: a handle operative to be grasped by a user; an arm extending outwardly from the handle; and moveable fins supported at a distal end of the arm, the fins being moveable between an unbiased position and a biased position; in the biased position, free ends of the fins having been moved toward each other such that an extent of the fins along a major axis is decreased relative to an extent of the fins along the major axis in the unbiased position.

6 Claims, 3 Drawing Sheets

(56) References Cited

U.S. PATENT DOCUMENTS

| | | | |
|---|---|---|---|
| 6,524,320 B2 * | 2/2003 | DiPoto | 606/108 |
| 7,198,598 B2 * | 4/2007 | Smith et al. | 600/114 |
| 7,214,186 B2 * | 5/2007 | Ritland | 600/217 |
| 7,226,413 B2 * | 6/2007 | McKinley | 600/210 |
| 7,625,374 B2 * | 12/2009 | Branch et al. | 606/84 |
| 7,648,512 B2 * | 1/2010 | Foley et al. | 606/105 |
| 7,815,649 B2 * | 10/2010 | Layne et al. | 606/105 |
| 7,887,565 B2 * | 2/2011 | Michelson | 606/246 |
| 8,100,917 B2 * | 1/2012 | Foley et al. | 606/105 |
| 8,388,525 B2 * | 3/2013 | Poo et al. | 600/206 |
| 2001/0010021 A1 | 7/2001 | Boyd et al. | |
| 2002/0049368 A1 * | 4/2002 | Ritland | 600/210 |
| 2002/0082604 A1 | 6/2002 | Abdelgany et al. | |
| 2002/0120346 A1 | 8/2002 | Boyer, II et al. | |
| 2002/0161449 A1 | 10/2002 | Muschler | |
| 2003/0032966 A1 * | 2/2003 | Foley et al. | 606/105 |
| 2003/0039676 A1 | 2/2003 | Boyce et al. | |
| 2003/0195520 A1 * | 10/2003 | Boyd et al. | 606/90 |
| 2003/0199874 A1 * | 10/2003 | Michelson | 606/61 |
| 2003/0236447 A1 * | 12/2003 | Ritland | 600/210 |
| 2004/0002711 A1 * | 1/2004 | Berry | 606/79 |
| 2004/0002712 A1 * | 1/2004 | Grinberg et al. | 606/79 |
| 2004/0138534 A1 * | 7/2004 | Ritland | 600/210 |
| 2004/0225228 A1 * | 11/2004 | Ferree | 600/554 |
| 2005/0107671 A1 * | 5/2005 | McKinley | 600/235 |
| 2005/0154396 A1 * | 7/2005 | Foley et al. | 606/90 |
| 2005/0154460 A1 * | 7/2005 | Yundt | 623/17.11 |
| 2005/0165408 A1 * | 7/2005 | Puno et al. | 606/99 |
| 2005/0228233 A1 * | 10/2005 | Ritland | 600/210 |
| 2006/0004261 A1 * | 1/2006 | Douglas | 600/210 |
| 2006/0052670 A1 * | 3/2006 | Stearns et al. | 600/216 |
| 2006/0084992 A1 * | 4/2006 | Michelson | 606/61 |
| 2006/0106462 A1 * | 5/2006 | Tsou | 623/17.16 |
| 2006/0142762 A1 * | 6/2006 | Michelson | 606/61 |
| 2006/0200138 A1 * | 9/2006 | Michelson | 606/61 |
| 2006/0200139 A1 * | 9/2006 | Michelson | 606/61 |
| 2006/0200164 A1 * | 9/2006 | Michelson | 606/90 |
| 2007/0038032 A1 * | 2/2007 | De Canniere et al. | 600/210 |
| 2007/0156020 A1 * | 7/2007 | Foley et al. | 600/104 |
| 2008/0108876 A1 * | 5/2008 | Houser et al. | 600/206 |
| 2008/0132764 A1 * | 6/2008 | Hamada | 600/201 |
| 2008/0221628 A1 * | 9/2008 | Milbocker et al. | 606/86 R |
| 2008/0255564 A1 * | 10/2008 | Michelson | 606/79 |
| 2008/0287955 A1 * | 11/2008 | Michelson | 606/90 |
| 2010/0241127 A1 * | 9/2010 | Foley et al. | 606/90 |
| 2011/0087231 A1 * | 4/2011 | Perri | 606/94 |
| 2011/0245620 A1 * | 10/2011 | Hamada | 600/219 |
| 2012/0197279 A1 * | 8/2012 | Perez-Cruet et al. | 606/170 |

FOREIGN PATENT DOCUMENTS

| | | |
|---|---|---|
| JP | 07222752 | 8/1995 |
| JP | 09149906 | 6/1997 |
| JP | 10211213 | 8/1998 |
| JP | 07051292 | 2/2005 |

* cited by examiner

DEVICES AND METHODS FOR TEMPORARILY RETAINING SPINAL ROOTLETS WITHIN DURAL SAC

BACKGROUND

1. Technical Field

The disclosure generally relates to spinal surgery.

2. Description of the Related Art

The human spine is composed of a column of thirty-three bones, called vertebrae, and their adjoining structures. The twenty-four vertebrae nearest the head are separate bones and are capable of individual movement. These vertebrae are generally connected by anterior and posterior longitudinal ligaments and by discs of fibrocartilage, called intervertebral discs, positioned between opposing faces of adjacent vertebral bodies. The remaining nine vertebrae are fused to form the sacrum and the coccyx and are incapable of individual movement. The vertebral body and the dorsal vertebrae enclose an opening termed the vertebral foramen, through which the spinal cord, a column of nerve tissue which communicates nerve impulses between the brain and the rest of the body, and spinal nerve roots pass and are protected from damage.

In this regard, FIG. 1 is a schematic diagram depicting three representative vertebrae (10, 12 and 14), associated intervertebral discs (16 and 18), spinal cord 20 and various spinal nerves (22, 24 and 26). In contrast, FIG. 2 depicts vertebrae 14 and the spinal cord 20 in greater detail. Specifically, an opening (e.g., a tear 28) in the dural sac 30, which surrounds the spinal cord, is evident. Notably, nerve rootlets (e.g., rootlet 32) extend from the opening, owing primarily to the outward flow of spinal fluid from the opening.

SUMMARY

Devices and methods for temporarily retaining spinal rootlets within a dural sac are provided. In this regard, an exemplary embodiment of a device comprises: a handle operative to be grasped by a user; an arm extending outwardly from the handle; and moveable fins supported at a distal end of the arm, the fins being moveable between an unbiased position and a biased position; in the biased position, free ends of the fins having been moved toward each other such that an extent of the fins along a major axis is decreased relative to an extent of the fins along the major axis in the unbiased position.

An exemplary embodiment of a method for temporarily retaining spinal rootlets within a dural sac comprises: providing a device having: a handle, an arm and moveable fins, the fins being supported at a distal end of the arm, the fins being moveable between an unbiased position and a biased position; inserting the fins into an opening in the dural sac such that the fins are positioned between the dural sac and the rootlets and such that the rootlets are retracted within the dural sac; closing a portion of the opening adjacent to a first of the fins; removing the fins from the dural sac; and closing a remaining portion of the opening.

Other systems, methods, features and/or advantages of this disclosure will be or may become apparent to one with skill in the art upon examination of the following drawings and detailed description. It is intended that all such additional systems, methods, features and/or advantages be included within this description and be within the scope of the present disclosure.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

DETAILED DESCRIPTION

Devices and methods for temporarily retaining spinal rootlets within a dural sac are provided, several exemplary embodiments of which will be described in detail. In this regard, reference is made to the schematic diagram of FIG. 3, which depicts an exemplary embodiment of such a device.

Figure 1:
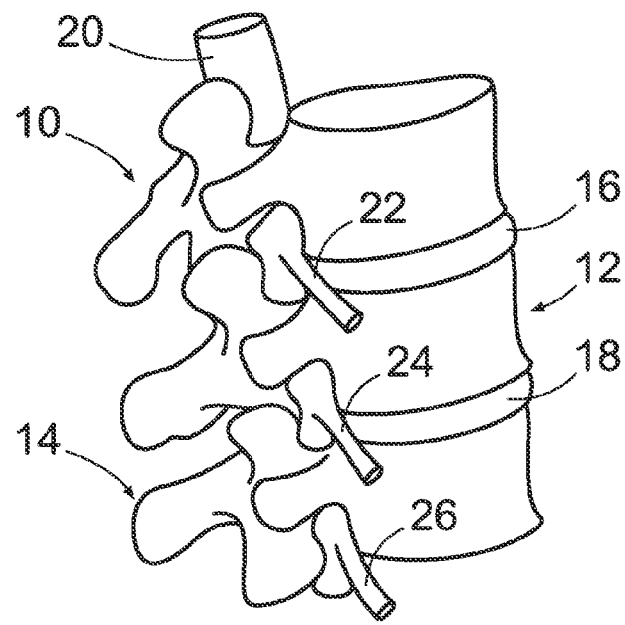
FIG. 1 is a schematic diagram depicting a representative portion of a spinal column.
Figure 2:
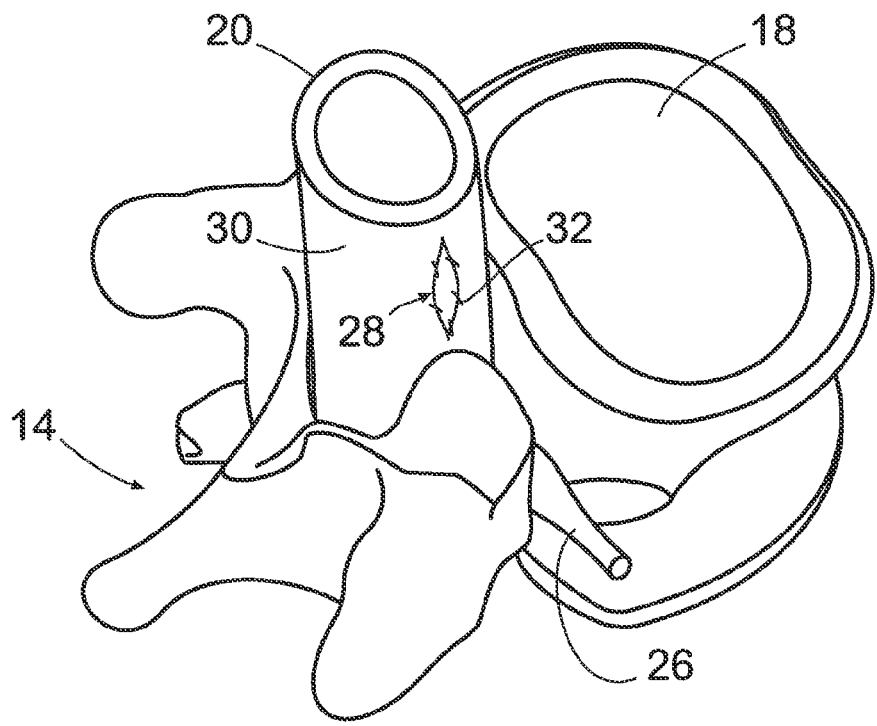
FIG. 2 is a schematic diagram depicting a portion of the spinal column of FIG. 1 in greater detail.
Figure 3:
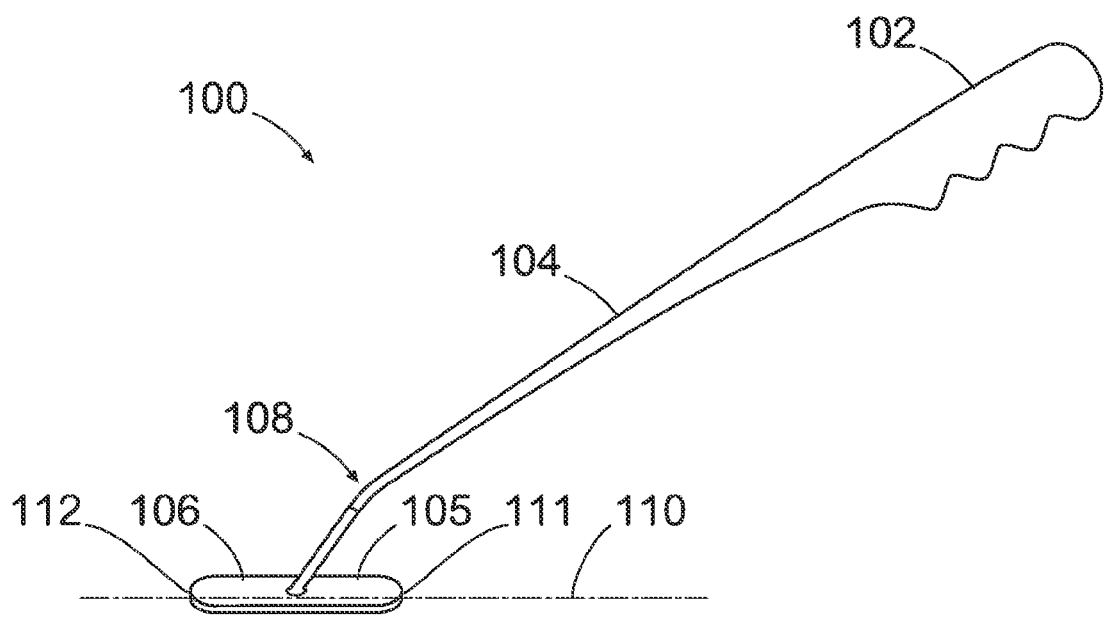
FIG. 3 is a schematic diagram depicting an exemplary embodiment of a device for temporarily retracting spinal rootlets within a dural sac.

As shown in FIG. 3, device 100 includes a handle 102, and arm 104 and moveable fins 105, 106. Handle 102 is operative to be grasped by a user. In this embodiment, various contours are provided that are adapted to complement and direct preferred finger placement although, in other embodiments, various other configurations can be used.

Arm 104 extends outwardly from the handle and exhibits a distal bend 108. In other embodiments, a straight arm configuration or a configuration that includes multiple bends can be used.

Moveable fins 105, 106 are supported at a distal end of arm 104 and extend generally along a major axis 110. The fins oppose each other in this embodiment and generally reside within a plane when in an unbiased position (depicted in FIG. 3). Additionally, each fin is generally rectangular although rounding of the edges may be preferable in some embodiments.

Fin 105 is a proximal fin (i.e., located closer to the handle) and fin 106 is a distal fin (i.e., located farther from the handle). In the embodiment of FIG. 3, arm 104 is inclined with respect to the fins such that an acute angle is formed between the proximal fin and the arm, and an obtuse angle is formed between the distal fin and the arm.

Fins 105, 106 are moveable between the unbiased position and a biased position. In the biased position, free ends (111, 112) of the fins are moved toward each other such that an extent of the fins along major axis 110 is decreased relative to the extent that the fins exhibit along the major axis when in the unbiased position. An example of fins moved toward a biased position is depicted in FIG. 4.

In the embodiment of FIG. 3, the fins are urged to the biased position by the material forming the fins. In this embodiment, the fins are formed of an inert silicone elastomer (e.g., SILASTIC®). As such, the fins are flexible, resilient and suited for medical use. Other materials can be used in other embodiments.

Figure 4:
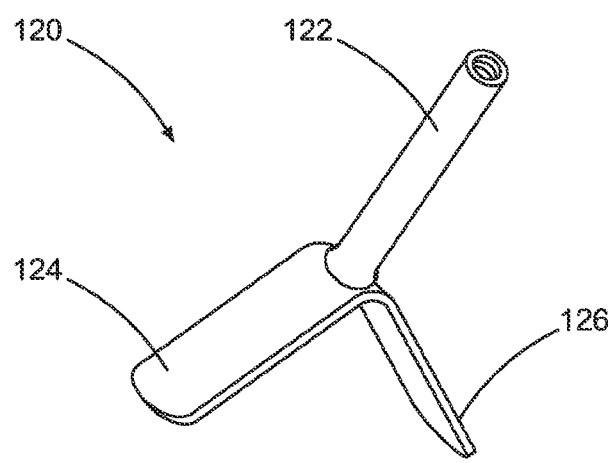
FIG. 4 is a schematic diagram depicting an exemplary embodiment of a replaceable fin assembly.

FIG. 4 is a schematic diagram depicting an exemplary embodiment of a replaceable fin assembly. That is, in contrast to the disposable version of the device depicted in FIG. 3, the fin assembly 120 of FIG. 4 is configured to removably attach and detach from a corresponding arm of a handle-arm assembly. As such, multiple fin assemblies (which may include different sizes of fins) can be used with a handle-arm assembly. After use, the handle-arm assembly can be sterilized and the fin assembly replaced.

In FIG. 4, fin assembly 120 includes a stem 122 that serves as an anchor for fins 124 and 126 (which are depicted in an intermediate position). Internal threads of stem 122 facilitate attachment of the fin assembly to a corresponding arm of a device. In other embodiments, various other configurations can be used to facilitate attachment and/or removal of a fin assembly.

Figure 5:
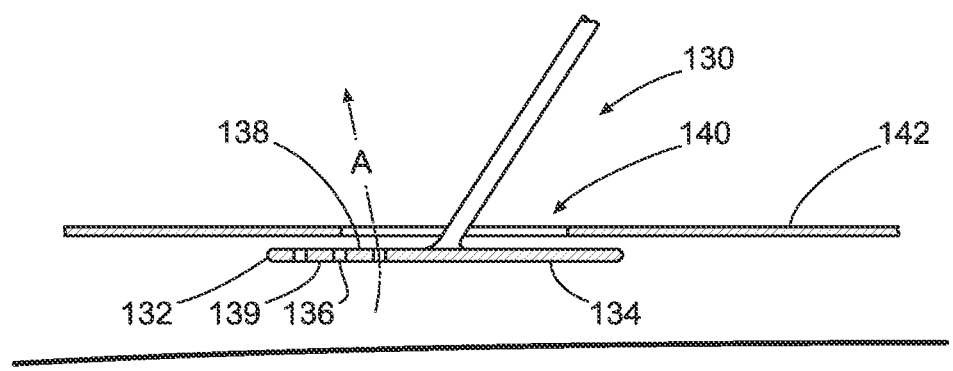
FIGS. 5 and 6 are schematic diagrams depicting an exemplary embodiment of a device with the associated fins being inserted into and used for temporarily retracting spinal rootlets within a dural sac.
Figure 6:
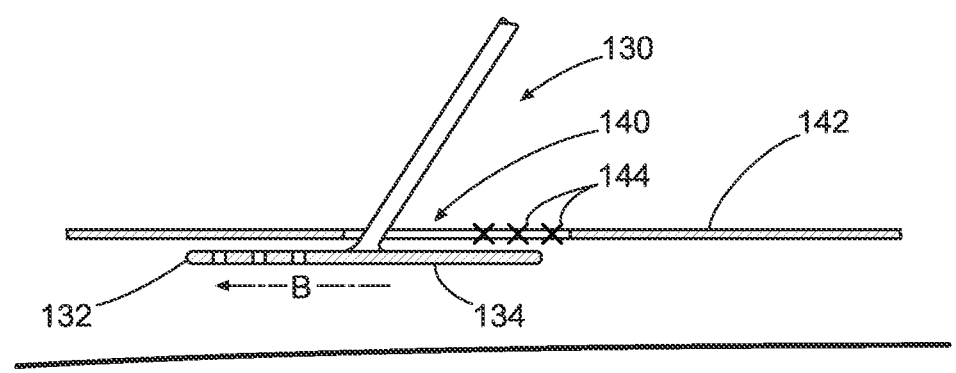

FIGS. 5 and 6 are schematic diagrams depicting an exemplary embodiment of a device with the associated fins being inserted into and used for temporarily retaining spinal rootlets within a dural sac. As shown in FIG. 5, device 130 includes a fins 132 and 134, with distal fin 132 incorporating holes (e.g., hole 136) that extend through the fin from the upper surface 138 to the lower surface 139. Note that, in this embodiment, fin 134 lack holes.

Also shown in FIG. 5, note that the fins 132, 134 are inserted into an opening 140 in the dural sac 142. This positions the fins between the dural sac and nerve rootlets so that the rootlets (not shown) are retained within the dural sac. Notably, retracting the rootlets within the dural sac with the device tends to reduce the potential for damaging the rootlets, such as during the repair of a dural tear. During a conventional repair, one or more instruments (e.g., a needle for suturing the tear) may be used in close proximity to the rootlets, thereby increasing the risk of damage to the rootlets. However, with the fins of the device being placed and forming a protective barrier between the dural sac and the rootlets, such damage may not occur.

It should be noted that the holes in the distal fin facilitate outward flow of spinal fluid (depicted by arrow A) through the opening 140. This directed flow of spinal fluid may facilitate a more efficient closing of opening 140 at a location adjacent the proximal fin 134, as fluid that may otherwise depart the opening in a vicinity of the proximal fin is reduced (i.e., rerouted toward the holes in the distal fin). In some embodiments, holes for directing spinal fluid may be concentrated toward the free end of a fin, although various other configurations can be used.

One manner of closing of the opening 140 is begun adjacent the proximal fin as depicted in FIG. 6. In this embodiment, closing is facilitated by sutures (e.g., suture 144). Notably, as the sutures encroach upon the stem of the device 130, the device is moved along the opening such as depicted by arrow B. As such, the fins form a movable barrier for protecting the nerve rootlets.

Figure 7:
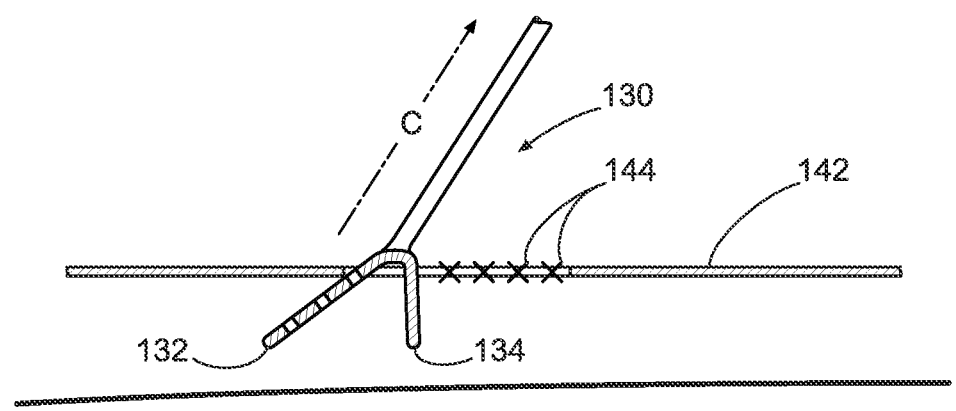
FIG. 7 is a schematic diagram depicting the exemplary embodiment of FIGS. 5 and 6 being removed from the dural sac.

As shown in FIG. 7, device 130 is removed from the dural sac so that a remaining portion of the opening 140 can be closed. Removal of the device includes drawing the arm away from the dural sac (as depicted by arrow C) so that free ends of the fins are moved toward each other (i.e., toward the biased position). This permits extraction of the fins from the remaining opening.

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

The invention claimed is:

1. A device for temporarily retaining spinal rootlets within a dural sac comprising:
   a handle operative to be grasped by a user;
   an arm extending outwardly from the handle; and
   an elongated flexible body configured to be inserted in an opening within a dural sac for positioning between spinal rootlets and said dural sac opening, whereby the rootlets are retained within said dural sac with said elongated flexible body creating a protective barrier to reduce potential damage to the rootlets, said elongated body traversable between a first position and at least one second position and defined by a first fin having an end region defining a first elongated flexible body terminal end and a second fin having an end region defining a second elongated flexible body terminal end, said elongated body formed from an inert flexible silicone elastomer allowing ease of removal from a partially sutured dural sac opening wherein said elastomer urges said terminal ends into the first position;
   wherein said first configuration, said elongated flexible body has a continuous, non-curved planar surface separating said first elongated flexible body terminal end and said second elongated flexible body terminal end, and wherein a distance between said first elongated flexible body terminal end and said second elongated flexible body terminal end is greater than when in said at least one second position;
   wherein opposing said terminal ends are movable towards each other into said second position by pressure from dural sac during removal position and being positioned at a greater distance away from a first configuration longitudinal axis of said elongated flexible body.

2. The device of claim 1, wherein at least one of said first fin or second fin has holes extending between an upper surface and a lower surface thereof.

3. The device of claim 2, wherein one of said first fin or said second fin lacks holes formed therethrough.

4. The device of claim 1, wherein:
   the arm is inclined with respect to said fins such that an acute angle is formed between at least one fin and the arm, and an obtuse angle is formed between said other fin and the arm.

5. The device of claim 1, wherein said terminal ends exhibit rounded edges.

6. The device of claim 1, wherein the fins are configured as a portion of a replaceable fin assembly operative to removably attach and detach from the arm.

* * * * *